United States Patent [19]

Barash et al.

[11] Patent Number: 4,839,352
[45] Date of Patent: * Jun. 13, 1989

[54] N-ACYL DERIVATIVES OF THIENAMYCIN

[75] Inventors: Louis Barash, Westfield; Burton G. Christensen, Metuchen; John Hannah, Matawan; William J. Leanza, Berkeley Heights; David H. Shih, Edison, all of N.J.

[73] Assignee: Merck & Co., Inc., Rahway, N.J.

[*] Notice: The portion of the term of this patent subsequent to Nov. 25, 1997 has been disclaimed.

[21] Appl. No.: 90,400

[22] Filed: Aug. 27, 1987

Related U.S. Application Data

[63] Continuation of Ser. No. 778,165, Sep. 18, 1985, abandoned, which is a continuation of Ser. No. 321,496, Nov. 16, 1981, abandoned, which is a continuation of Ser. No. 160,718, Jun. 18, 1980, abandoned, which is a continuation of Ser. No. 861,247, Dec. 16, 1977, abandoned, which is a continuation of Ser. No. 733,653, Oct. 18, 1976, abandoned, which is a continuation of Ser. No. 634,291, Nov. 21, 1975, abandoned.

[51] Int. Cl.$^4$ .................. C07D 487/04; A61K 31/40
[52] U.S. Cl. ..................................... 514/210; 540/350
[58] Field of Search ............... 540/310, 350; 514/192, 514/195, 210

[56] References Cited

U.S. PATENT DOCUMENTS

| | | | |
|---|---|---|---|
| 3,950,357 | 4/1976 | Kahan et al. | 260/326.27 |
| 4,000,161 | 12/1976 | Goegelman et al. | 260/326.31 |
| 4,162,324 | 7/1979 | Cassidy et al. | 424/274 |
| 4,165,379 | 8/1979 | Kahan et al. | 260/245.2 T |
| 4,194,047 | 3/1980 | Christensen et al. | 546/272 |
| 4,226,870 | 10/1980 | Christensen et al. | 424/263 |
| 4,234,596 | 11/1980 | Christensen et al. | 424/274 |
| 4,235,917 | 11/1980 | Christensen et al. | 424/274 |
| 4,235,920 | 11/1980 | Christensen et al. | 424/214 |
| 4,235,967 | 11/1980 | Cassidy et al. | 435/119 |
| 4,397,861 | 8/1983 | Christensen et al. | 424/274 |

FOREIGN PATENT DOCUMENTS

| | | |
|---|---|---|
| 1467413 | 3/1977 | United Kingdom . |
| 1483142 | 8/1977 | United Kingdom . |

OTHER PUBLICATIONS

Journal of Heterocyclic Chemistry, vol. 20, pp. 787–789 D. Schmidt, et al.
Chem. Pharm. Bull., p. 4573.
Organic Chemistry, 2nd. Ed., R. Morrison & R. Boyd, Allen and Bacon & Co. pp. 751–753.
"The Chemistry of Amides", Ed. J. Zabick, Interscience Publishers, 1970, Chapter 7, titled "Chemistry of Imdic Compounds" by O. H. Wheeler and O. Rosatto.

Primary Examiner—Nicholas S. Rizzo
Attorney, Agent, or Firm—Robert J. North; Hesna J. Pfeiffer

[57] ABSTRACT

Disclosed are N-acyl derivatives of the antibiotic thienamycin having the following structural formula:

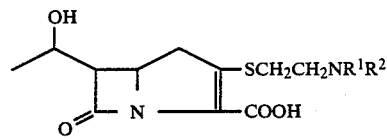

wherein $R^1$ and $R^2$ are independently selected from the group consisting of hydrogen and acyl. Such derivatives and their pharmaceutically acceptable salts, are useful as antibiotics. Also disclosed are processes for the preparation of such derivatives, pharmaceutical compositions comprising such derivatives, and methods of treatment comprising administering such derivatives and compositions when an antibiotic effect is indicated.

12 Claims, No Drawings

N-ACYL DERIVATIVES OF THIENAMYCIN

BACKGROUND OF THE INVENTION

This application is a continuation of 778,165 filed Sept. 18, 1985, now abandoned, which is a continuation of 321,496 filed Nov. 16, 1981, now abandoned, which is a continuation of 160718 filed June 18, 1980, now abandoned, which is a continuation of 861,247 filed Dec. 16, 1977, now abandoned, which is a continuation of 733,653 filed Oct. 18, 1976, now abandoned, which is a continuation of 634,291 filed Nov. 21, 1975, now abandoned.

This invention relates to novel N-acyl derivatives of the antibiotic thienamycin. Such derivatives and their pharmaceutically acceptable salts are useful as antibiotics. This invention also relates to processes for the preparation of such compounds, pharmaceutical compositions comprising such compounds, and methods of treatment comprising administering such compounds and compositions when an antibiotic effect is indicated.

Thienamycin, the starting material required for preparation of the compounds of the present invention, is disclosed and claimed in co-pending, commonly assigned U.S. patent application Ser. No. 526,992, filed Nov. 25, 1974 (now U.S. Pat. No. 3,950,357, issued Apr. 13, 1976); said application is incorporated herein by reference for the disclosure relative to the preparation and isolation of thienamycin. Thienamycin is known to have the following structural formula:

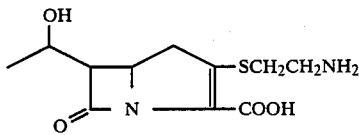

I

Thienamycin and all of its isomers (in pure form and as mixtures) are also obtainable by the total synthesis disclosed and claimed in co-pending, commonly assigned U.S. patent application Ser. No. 833,210 (Sept. 15, 1977). This application is incorporated herein by reference to the extent that it makes available all isomers of I as starting materials in the preparation of the compounds of the present invention.

The N-acyl thienamycin derivatives of the present invention may be depicted by the following generic structural formula (II):

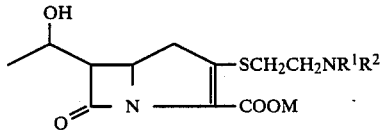

II or more conveniently by the symbol (II):

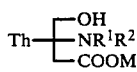 

II wherein "Th" symbolizes the bicyclic nucleus of thienamycin and the OH, amino and carboxyl groups of thienamycin are illustrated;

M is H, a salt cation selected from the alkali or alkaline earth metals such as sodium potassium or calcium or an amine salt, such as $NH_3$, $N(R)_3$ wherein R is alkyl having 1 to 6 carbon atoms, and the like;

$R^1$ and $R^2$ are independently selected from the group consisting of hydrogen ($R^1$ and $R^2$ are not both hydrogen) or an acyl group. The most preferred compounds of this invention are those wherein $R^1$ is hydrogen and $R^2$ is acyl. The term "acyl" is by definition inclusive of the alkanoyls including derivatives and analogues thereof such as thio analogues wherein the carbonyl oxygen is replaced by sulphur, diacyl radicals wherein $R^1$ and $R^2$ are joined together; as well as the sulphur and phosphorous acyl analogues such as substituted sulfonyl-, sulfinyl-, and sulfenyl-radicals, and substituted P(III) and P(V) radicals such as the substituted phosphorous-, phosphoric-, phosphorous- and phosphonic radicals, respectively. Such acyls radicals of the present invention are further defined below.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as N-acyl derivatives thereof. These antibiotics are active against a broad range of pathogens which representatively include both gram positive bacteria such as *S. aureus*, *Strep.pyogenes* and *B. subtilis* and gram negative bacteria such as *E. coli*, *Proteus morganii*, *Serratia* and *Klebsiella*. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

In the generic representation of the compounds of the present invention (II, above), the acyl radical represented by either $R^1$ or $R^2$ can, inter alia, be substituted or unsubstituted aliphatic, aromatic or heterocyclic, araliphatic or heterocylylaliphatic carboxylic acid radical, a substituted or unsubstituted carbamyl radical or a carbothioic acid radical. One group of acyl radicals can be represented by the general formula:

$$-\overset{\overset{X}{\|}}{C}-R''$$

wherein X is O or S and R" represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms;

arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroalkyl group (mono- and bicyclic) wherein the alkyl moiety typically comprises 1 to 3 carbon atoms and the heterocyclic ring comprises typically 4–10 atoms and the hetero atom or atoms are selected from O, N and S; such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-d -isoxa.olyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridiylmethyl, 5-iosxazolylmethyl, 4-methoxy-5-isoxazolylmethyl, 4-methyl-5-isoxazolylmethyl, 1-imidazolymethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)-methyl, 2- or 3-(5-methylthienyl)-methyl, 2- or 3-(methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl) methyl, 2-furylmethyl, 2-(5-nitrofuryl)methyl, 3-furylmethyl, 2-theinylmethyl, 3-thienylmethyl, tetrazolylmethyl benzamidinomethyl and cyclohexylamidinomethyl The acyl group can also be a radical of the formula:

wherein X is O or S and n is 0–4, Z represents oxygen, sulfur, carbonyl or nitrogen and R" is defined as above.

Representative members of the substituent

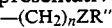

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

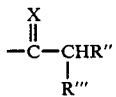

wherein R" is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, αo-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D-(—)-α-amino-3-chloro-4-hydroxybenzyl, α-amino(-cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(-)-2-thienyl-guanidinomethyl, D(-)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxy-methyl, 3-(1,2-thiazolyl)-aminomethyl 3-(1,2-thiazolyl)-hydroxymethyl, 3-(1,2-thiazolyl)-carboxymethyl, 2-(1,4-thiazolyl)- aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, aminoethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl-3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl substituent $R^1$ and $R^2$ may also be selected from sulphur (1) and phosphorous (2) radicals:

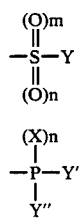

wherein with respect to (1), m and n are integers selected from 0 or 1 and $Y = O^\ominus M^\oplus$, $-N(R'')_2$, and $R''$; wherein $M^\oplus$ is selected from hydrogen alkali metal cations and organic bases; and $R''$ is as defined above, e.g., alkyl, alkenyl, aryl and heteroaryl. With respect to (2) X=O or S; n=0 or 1; and Y' and Y'' are selected from the group consisting of $O^\ominus M^\oplus$, $-N(R'')_2$, R'' and ZR'' wherein all symbolism is as defined above, e.g., R'' and ZR'' are representatively: alkyl, alkenyl, aryl, heteroaryloxy; Y' and Y'', including R''' moieties, can be joined together to form cyclic ester, ester- amide and amide functions. Illustrative examples of (1) are N-(methylsulphonyl)thienamycin, N-(o-nitrophenylsulphonyl)thienamycin, N-(p-chlorophenylsulphinyl)-thienamycin, N-(o-nitrophenylsulphenyl)thienamycin, N-sulphamoylthienamycin, N-dimethylsulphamoyl-thienamyc and thienamycin N-sulphonic acid sodium salt. Illustrative examples of (2) are N-(dimethoxyphosphino)thienamycin, N-(dibenzyloxyphosphino)thienamycin, N-(dihydroxyphosphino)thienamycin disodium salt, N-(dimethoxyphosphinyl)thienamycin, N-(dimethoxyphosphinothioyl)thienamycin, N-(dibenzylphosphinyl)thienamycin, N-(dihydroxyphosphinyl)thienamycin disodium salt.

An acyl class of particular interest is those acyl radicals, $R^1$ and $R^2$ of Structure II, above, which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl and t-butyldimethylsilyl are also of interest.

The following radicals, according to the foregoing definition of acyl (radicals $R^1$ and $R^2$ of Structure II, above), are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanylthioacetyl, guanidinoacetyl, 3-guanidinopropionyl, $N^3$-methylguanidinopropionyl, hydroxyacetyl, 3-hydroxypropionyl, acryloyl, propynoyl, malonyl, phenoxycarbonyl, amidinoacetyl, acetamidoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)-propionyl, 3-(5-aminoimidazol-1-yl)propionyl, 3-methyl-1-imidazoliumacetyl, 3-sydnonylacetyl, o-aminomethylbenzoyl, o-aminobenzoyl,

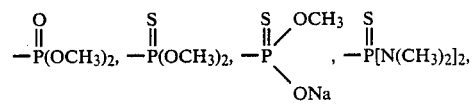

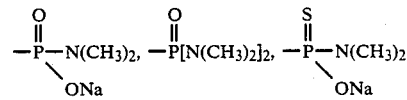

An especially preferred class of acyl radicals (R¹ and R² of structure II, above) are terminally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such preferred substituted acyls may be represented by the following formula:

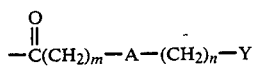

wherein m, and n are integers selected from 0 to 5; A is O, NR' (R' is hydrogen or loweralkyl having 1-6 carbon atoms), S or A represents a single bond; and Y is selected from the following group:

1. amino or substituted amino $-N(R)_2$ and $-N^+(R)_3$ wherein the values for R are independently selected from: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms; two R groups may be joined together with the N atom to which they are attached to form a ring having 3-6 atoms.

2. amidino and substituted amidino

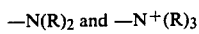

wherein the value of R is independently selected from the group consisting of: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

3. guanidino and substituted guanidino

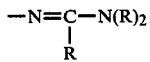

wherein R is as defined in 2. (above).

4. guanyl and substituted guanyl

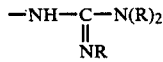

wherin R is as defined in 2. (above).

5. nitrogen-containing mono- and bicylic heterocycles (aromatic and non-aromatic) having 4 to 10 nuclear atoms wherein the hetero atom or atoms, in addition to nitrogen, are selected from oxygen and sulphur. Such heterocycles are representatively illustrated by the following list of radicals (R' is H or loweralkyl having 1-6 carbon atom):

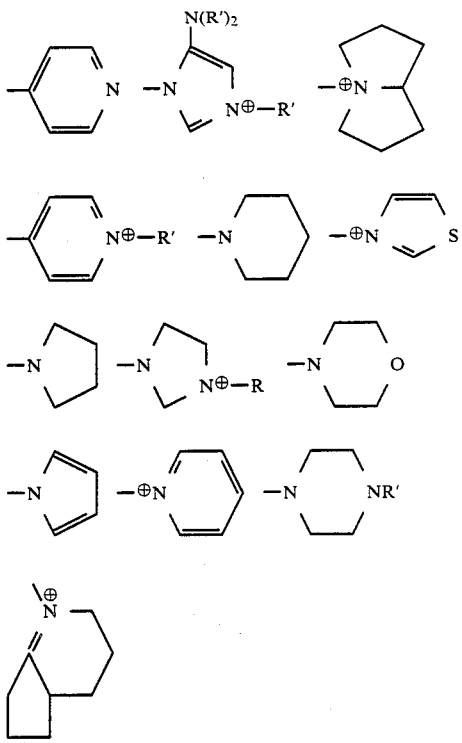

The following specific acyl radicals falling within this class are additionally representative and are preferred:

-continued

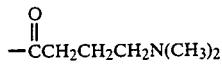

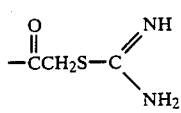

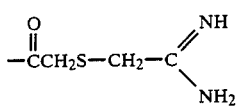

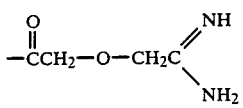

However, it is to be understood that any acyl radical may be employed in the practice of the invention and is to be considered within the scope of the invention.

In general the compounds of the present invention are prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester.

The acylation reaction may be conducted at a temperature in the range of from about $-20°$ C. to about $100°$ C. but is preferably conducted at a temperature in the range of from $-8°$ C. to $25°$ C. Any solvent in which the reactants are soluble and substantially inert may be employed, for example, polar solvents such as water, alcohols and polar organic solvents in general such as dimethylformamide (DMF), hexamethyl phosphoramide (HMPA), acetone, dioxane, tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

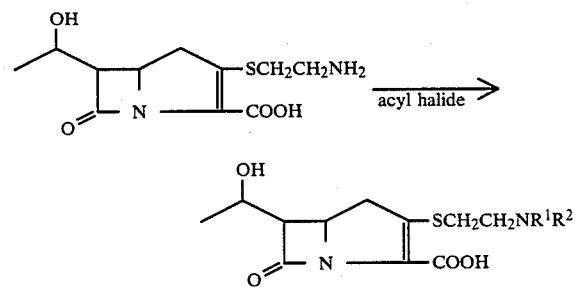

Generally when the above-described acylating reaction employs an acid halide (suitable halides are chloro, iodo or bromo) or anhydride the reaction is conducted in water or an aqueous mixture of a polar solvent such as acetone, dioxane, THF, DMF, acetonitrile or the like in the presence of a suitable acceptor base such as $NaHCO_3$, $MgO$, $NaOH$, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin are suitable for this purpose. Silylation of thienamycin proceeds rapidly to give the tris-triorganosilyl derivative, for example tris-trimethylsilyl thienamycin, $Th-(TMS)_3$:

Such derivatives, which are readily soluble in organic solvents, are conveniently prepared by treating Thienamycin with an excess of hexamethyldisilazane and a stoichiometric amount of trimethylchlorosilane at 25° C. with vigorous stirring under a $N_2$ atmosphere.

The products of this invention (II) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, hydrobromic, sulfuric, nitric, toluene-p-sulphonic and methane sulphonic acids may also be employed, in such instances where the acyl radical contains a basic group.

The salts can be mono-salts such as the monosodium salt obtained by treating one equivalent of sodium hydroxide with one equivalent of the product (II), also mixed di-salts. Such salts may be obtained by treating one equivalent of a base having a divalent cation, such as calcium hydroxide, with one equivalent of the product (II). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel thienamycin derivatives of the present invention are valuable antimicrobial substances which are active against various gram-positive and gram-negative pathogens such as *Bacillus subtilis, Salmonella schottmuelleri* and *Proteus vulgaris*. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli., Strep. pyogenes, Klebsiella pneumoniae, Bacillus subtilis, Salmonella typhosa, Pseudomonas* and *Bacterium proteus*. The antibacterials of the invention may further be utilized as additives to animal feedstuffs, for preserving food and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be adminstered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl n-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder, liquid sprays, inhalants, lozenges and throat paints. For medication of the eyes or ears, the preparations may be presented as individual capsules, in liquid or semi solid form, or may be used as drops. Topical applications may be formulated in hydrophobic or hydrophilic bases as ointments, creams, lotions, paints and powders.

Also, in addition to a carrier, the instant compositions may include other ingredients such as stabilizers, binders, antioxidants, preservatives, lubricators, suspending agents, viscosity agents for flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit doage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 100 mg. In parenteral administration the unit dosage is usually the pure compound in a slightly acidified sterile water solution or in the form of a soluble powder intended for solution.

In the following Examples, which further illustrate but do not limit the product, process, compositional or method of treatment aspects of the present invention, the compounds of the present invention will be designated by the previously introduced symbol:

wherein the three functional groups are illustrated.

EXAMPLE 1

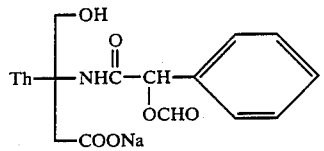

Preparation of N-(O-formyl)-D-mandeloylthienamycin Sodium Salt

To thienamycin (40 mg.) in 10 ml. water is added successively at 0° C., 124 mg. NaHCO₃, 8 ml. dioxane and then with stirring 1.2 equivalent N-(O-formyl)-1-mandelolyl chloride over a period of one minute. After six minutes total reaction time, the mixture is extracted three times with cold ethyl ether. Electrophoresis of an aqueous portion (0.05M, pH 7, aqueous phosphate buffer, 50 V/cm., 20 minutes) shows 67% conversion to desired product. The pH is adjusted to 2.2 with 1M H₃PO₄ solution and the solution is extracted three times with ethyl acetate. The ethyl acetate (EtOAc) solution is dried over MgSO₄ and extracted twice with two equivalents of NaHCO₃ solution. The aqueous extract, lyophilized, contains 164 optical density units (ODU), at 302 nm by uv analysis at pH 7.0, of which 95% is extinguished after treatment with hydroxylamine for one hour. The yield is 53%. Electrophoresis as before shows one spot by bioautograph, 4 cm towards the anode. NMR (δD₂O) 1.30 (d, J=6 Hz), CH₃CH; 2.8–3.7 (m, CH₂), 4.0–4.5 (m, CH β-lactam), 4.73, HDO; 5.97 (s, C₆H₅CHOCHO), 7.53 (s, C₆H₅), 8.30 (s, C₆H₅CHOCHO).

EXAMPLE 2

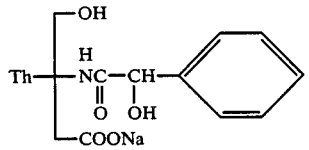

Preparation of N-D-Mandeloylthienamycin Sodium Salt

The title compound is made following the procedure of Example 1, but before EtOAc extraction the aqueous extract is allowed to stand at 25° C. for one hour. Electrophoresis (50 V/cm., 20 min., pH 7, aqueous phosphate, 0.05M) shows one spot by bioautograph, 4 cm. towards the anode, NMR (δ, D₂O) 1.50 (d, J=6 Hz, CH₃CH); 2.8–3.8 (m, CH₂), 4.2–4.6 (m, CH β-lactam); 4.96 (s, HDO); 5.40 (s, C₆H₅CH$^{OH}$).

EXAMPLE 3

N-Propionylthienamycin Sodium Salt

To Thienamycin, (25 mg. in 6 ml. water at 0° C.) is successively added 38.6 mg. NaHCO₃, 5 ml. dioxane and then with stirring one equivalent of propionic anhydride over a period of 3 min. After 10 min., the mixture is extracted three times with cold ethyl ether. Electrophoresis of the aqueous (aq.) extract (0.05M, pH 7, phosphate buffer, 50 V/cm., 20 min.) shows no free Thienamycin present. The aq. extract is adjusted to pH 6.8 and contains 600 ODU at 302 nm by uv analysis which is 95% extinguished after treatment with hydroxylamine for one hour. NMR (δ, D₂O) 1.42 (m CH₂CH₃, CH₃CH); 2.48 (q, CH₂CH₃); 2.86–2.90 (m, CH₂), 4.30–4.70 (m, CH β-lactam), 4.86 (HDO).

EXAMPLE 4

N-(Methoxyacetyl)thienamycin Sodium Salt

To Thienamycin, (55 mg. in 6 ml. water at 0° C.), is added successively 68 mg. NaHCO₃, 6 ml. dioxane and with stirring 1.1 equivalents methoxyacetylchloride over a period of 1.5 minutes. The mixture is stirred an additional 10 minutes. The mixture is extracted three times with cold ethyl ether. Electrophoresis of aq. extract (0.05M, pH 7 phosphate buffer, 50 V/cm., 20 min.) shows no free Thienamycin present. The aq. extract, adjusted to pH 6.8, contains 105 ODU at 302 nm. by uv analysis, which is 95% extinguished after treatment with hydroxylamine for one hour. NMR (δ, D₂O) 1.56 (m, CHCH₃), 2.84–3.60 (CH₂), 3.72 (s, OCH₃), 4.29 (s, OCH₂), 4.98 (s HDO).

EXAMPLE 5

N-(p-Nitrobenzyloxycarbonyl)thienamycin Lithium Salt

To Thienamycin (220 mg. in 60 ml. water at 0° C.), is added successively, 679 mg. NaHCO₃, 60 ml. dioxane and then with stirring 1.1 equivalents p-nitrobenzylchloroformate over a period of 1.5 minutes. The mixture is allowed to react 10 minutes, and is then extracted three times with cold ethyl ether. Electrophoresis (0.05M, pH 7, phosphate buffer, 50 V/cm., 20 minutes) shows no free Thienamycin present. The aq. extract is adjusted to pH 2.2 with 1M H₃PO₄ solution and extracted three times with EtOAc. The EtOAc extract is dried over MgSO₄, filtered and reextracted 0.1N LiOH, to pH 8.2. The final pH is adjusted to 7.0 with 1M H₃PO₄ and the sample lyophilized. The yield is 205 mg. (54%).

EXAMPLE 6

Preparation of N-(o-Nitrobenzyloxycarbonyl)thienamycin Sodium Salt

To Thienamycin (43 mg. at 0° C.) is added 1:1 tetrahydrofuran-H₂O (10 ml.). The mixture is rapidly stirred while 132 mg. NaHCO₃ (10 equiv.) is added, and then, dropwise with stirring over 2 min., four equivalents of o-nitrobenzylchloroformate is added. After thirty minutes, the pH is adjusted to 7 with 25% H₃PO₄ and the solution extracted three times with ether. The aqueous portion is evaporated in vacuo at 25° C. temperature and is then brought to pH 2.2 at 0° C. Solid NaCl is added and then the cold acidic solution is extracted three times with cold EtOAc. The EtOAc extracts are combined and quickly back washed with cold brine, dried with anhydrous MgSO₄, filtered and back extracted with 10 ml. of water containing 1.7 equivalents of solid NaHCO₃. The extract is lyophilized in vacuo at ambient temperature and contains 366 ODU at 303 nm by uv analysis in H₂O at pH 7.0, which is 95%

EXAMPLE 7

Preparation of N-(Trichloroethoxycarbonyl)thienamycin Lithium Salt

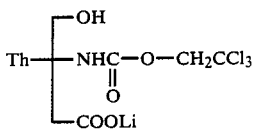

To Thienamycin (40 mg. in 18 ml. 1:1 THF-H$_2$O at 0° C.) is added while stirring 225 mg. (15.2 equiv.) NaHCO$_3$, and then, dropwise with stirring over 2 min., 1.8 equivalents of trichloroethylchloroformate dissolved in 0.6 ml. THF. After 6 minutes the pH is adjusted to 7.2 with 25% H$_3$PO$_4$ and the solution is extracted with ether. The aqueous portion after removing any entrained ether in vacuo is then brought to pH 2.5 at 0° C. and extracted with cold EtOAc. The ethyl acetate extracts are combined quickly backwashed with cold brine, dried with anhydrous MgSO$_4$, filtered and back extracted with 0.01M LiOH to pH 6.8. The aqueous extract is freed from any EtOAc in vacuo and lyophilized. The residual solid contains 936 ODU (39.7%) by uv analysis at 302 nm which is 90% extinguished after treatment with hydroxylamine for one hour in 0.05M phosphate buffer (pH 7). The yield is 32 mg. Electrophoresis (50 v/cm, 20 min., pH 7 0.05M phosphate) exhibits one zone by bioautograph (MB 108, *staph. aureus*), 2.4 cm toward the anode. Liquid chromatograph on C$_{18}$ Bondapak (Waters Assoc.) in aq. 10% THF exhibits one main peak free of any unreacted Thienamycin.

EXAMPLE 8

Preparation of N-Bromoacetylthienamycin

To a cooled solution of Thienamycin (20.0 mg) and sodium bicarbonate (0.3 g.) in 10 ml. of water and 8 ml. of dioxane is added with stirring a solution of 0.25 g. of bromoacetic anhydride in 2 ml. dioxane over a period of 20 min. The pH is maintained at 8–8.3. The mixture is stirred for an additional 10 minutes, layered with ether, and neutralized to pH 7 by the addition of 8% phosphoric acid. The ethereal layer is separated and the aqueous layer is extracted twice again with ether. The aqueous layer is evaporated under reduced pressure to 0.5 ml., diluted to 2 ml. with water and put on 50 ml. of XAD-2 resin. The column is eluted with water. The first 80 ml. is discarded, then the next 100 ml. is collected. The solvent is changed to 10% THF and an additional 100 ml. collected. The combined eluates are adjusted to pH 7, evaporated to 5 ml. under reduced pressure and freeze-dried to give the sodium salt of N-bromoacetylthienamycin in 60% yield. UVλ$_{max}$ 302 mμ.

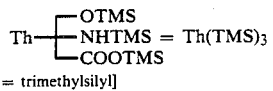

[TMS = trimethylsilyl]

Preparation of Silylated thienamycin

Thienamycin (80.0 mg.) is suspended in 40 ml. tetrahydrofuran (THF) under a N$_2$ atmosphere and is concentrated to 10 ml., hexamethyldisilazane (1.0 ml.) and trimethylchlorosilane (300 μl) is added. The mixture is reacted for 20 mins. at 25° C., with vigorous stirring. The suspension is then centrifuged to remove ammonium chloride. The supernatant is evaporated to an oil under a nitrogen stream for future reaction.

EXAMPLE 10

Preparation of N-(O-nitrobenzyloxycarbonyl)thienamycin via Th(TMS)$_3$

To Th(TMS)$_3$ (24 mg.) in 0.8 ml. dry THF is added 23 mg. of o-nitrocarbobenzyloxy chloride followed by 0.015 ml. of triethylamine. After vibromixing for 30 minutes at 25° C., the mixture is concentrated to dryness in a stream of dry N$_2$. The pasty residue is washed three times with petroleum ether. The residue is stirred with a mixture of 1.5 ml. THF and 10 ml. of pH 7 phosphate buffer for 20 mins. then charged to a column (30 ml.) of Dowex 50 (Na$^+$) resin. The column is eluted with water and the effluent monitored by UV absorption at 302 nm. The fractions containing the product are combined and freeze-dried.

EXAMPLE 11

Preparation of N-(p-methoxybenzyloxycarbonyl)thienamycin Sodium Salt (I) and Lithium Salt (II)

To Thienamycin (20 mg. in 5 ml. water at 0° C.) is added 105 mg. NaHCO$_3$ (20 equiv.), 5 ml. dioxane, and then, dropwise with stirring over 1 min., the pH is adjusted to 7.5 with 1M H$_3$PO$_4$ and the solution extracted three times with ether. The aqueous portion is then adjusted to pH 2.2 at 0° C. and extracted three times with EtOAc. The EtOAC is dried quickly with MgSO$_4$, filtered, and extracted with a few ml. water containing 6.3 mg. NaHCO$_3$. The first extract, lyophilized, contains 172 ODU at 303 nm by UV analysis in H$_2$O at pH 7.0, which is 95% extinguished after treatment with hydroxylamine for one hour. The yield of I is 16 mg. Electrophoresis (50 v/cm, 20 min., pH 7 phosphate buffer) shows one spot by bioautograph, 4 cm towards the anode. NMR (δ, D$_2$O): 1.49 (d, J=6 Hz, CH$_3$CH); 2.8–3.7 (m, CH$_2$); 3.99 (s, OMe); 4.0–4.6 (m, β-lactam CH); 4.92 (s, HDO); 5.20 (s, OCH$_2$); 7.13 (d, J=8 Hz, C$_6$H$_4$).

Extracting the EtOAc solution with 0.1N LiOH to pH 7.8 and lyophilizing gives the Lithium Salt II. The spectral and electrophoretic properties of II are the same as those of I.

EXAMPLE 12

Preparation of N-Azidoacetylthienamycin Sodium (I) and Lithium (II) Salts

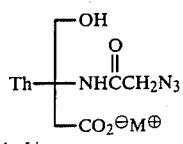

M = Na, Li

Thienamycin (48 mg., 0.18 mmol) is dissolved in 10 ml. cold water and is kept at 0° C. To the solution is added sodium bicarbonate (147 mg., 17.6 mmol) and dixoane (10 ml.). Azidoacetyl chloride (60 mg., 0.05 mmol) is added to the solution during a period of 2 min. The reaction mixture is stirred for 15 min. and then is neutralized to pH 7.0 with 30% phosphoric acid and is transferred into a separatory funnel. The solution is extracted with 2×50 ml. ether. The aqueous layer is concentrated to 5 ml. and then is charged to a Dowex AG-50×8 (sodium form) ion exchange column. The desired fractions, monitored by U.V., are combined and lyophilized to give 21 mg. of the product (I).Electrophoresis(50 V/cm., 20 min. in pH 7.0 phosphate buffer) of the product shows a single bio-active band which moves 4 cm. towards the anode. UV$\lambda_{max}^{H2O}$ 300 nm; Pmr (100 MHz, D$_2$O): 1.26 (d, CH$_3$CH), 2.92–3.43 (m, 3CH$_2$ and C$_6$-H), 4.01 (s, CH$_2$N$_3$) and 4.20 ppm (m, C$_5$-H and C$_7$-H).

Thienamycin (76.2 mg., 0.28 mmol) is dissolved in 10 ml. of cold water and is kept at 0° C. To the solution is added 0.6 ml. of 1.0N lithium hydroxide solution and 10 ml. dioxane. After stirring for 1 min., azidoacetyl chloride (33.6 mg., 0.28 mmol) is added during a period of 2 min. The reaction mixture is stirred for an additional one minute then is neutralized to pH 7.0 with 30% phosphoric acid. After extraction with ether, the aqueous solution is concentrated to 5 ml. and is charged to the Dowex AG-50wx8 (lithium form) ion exchange column. The desired fractions, monitored by U.V., are combined and lyophilized to give 38 mg. of the product (II). UV$\lambda_{max}^{H2O}$ 300 nm.

EXAMPLE 13

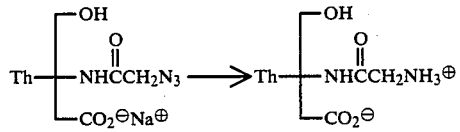

Preparation of N-Glycyl-thienamycin

Platinum oxide (60 mg.) and 2 ml. water are placed in a hydrogenation flask and stirred under 1 atm. hydrogen at 25° C. for 20 minutes. To the flask is added N-azidoacetyl thienamycin sodium salt (6.0 mg. 0.02 mmol in 4 ml. water). The reaction mixture is stirred at 25° C. under 1 atm. hydrogen for 30 minutes. The resulting mixture (pH 8.7) is adjusted to pH 7.0 with 30% phosphoric acid and filtered from the catalyst. The aqueous solution is concentrated to 2 ml. and then is charged to the Dowex AG-50w×8 (sodium form) ion exchange column. The desired fractions, monitored by U.V., are combined and lyophilized to give 3.8 mg. of the product. The electrophoresis (50 v/cm, 20 min.) of the product in pH 7.0 phosphate buffer shows one single bioactive band at the origin. UV$\lambda_{max}^{H2O}$ 300 nm; Pmr (100 MHz, D$_2$O): δ1.27 (d, CH$_3$CH), 2.96–3.37 (m, 3CH$_2$ and C$_6$-H), 3.70 (s, COCH$_2$NH$_2$), and 4.20 ppm (m, C$_5$-H and C$_7$-H).

EXAMPLE 14

Preparation of N-Benzyloxycarbonylthienamycin

A solution of 14 mg. of Thienamycin in 4 ml. of 0.05M pH 7 phosphate buffer and 2 ml. of dioxane in a 3-necked flask fitted with a stirrer, thermometer, pH electrode and the delivery tip of an automatic titrator is cooled to −0° C. in a methanol-ice bath. The pH is brought to 8.2 by the addition of 0.2N sodium hydroxide in 50% aqueous dioxane and a solution of 0.015 ml. of carbobenzyloxy chloride in 2 ml. of dioxane is added. The mixture is stirred at −6° C., pH 8.2, for ten minutes, then layered with ether and adjusted to pH 7 by the addition of hydrochloric acid. The layers are separated by centrifugation and the aqueous phase is extracted twice again with ether. The aqueous phase is layered with ethyl acetate and acidified to pH 2. The ethyl acetate is separated and the aqueous layer is extracted again with ethyl acetate. The combined ethyl acetate layer is washed with saturated sodium chloride solution, dried over magnesium sulfate and filtered. The filtrate is stirred with water and the pH brought to 7 by the addition of dilute sodium bicarbonate solution. The aqueous phase is separated and freeze dried giving the sodium salt of N-benzyloxycarbonylthienamycin, 10 mg. (46%). The UV spectrum, $\lambda_{max}$ 303 mμ, E% 147 (ε6,290) indicates about 80% purity. Electrophoresis at 50 V/cm for 20 min. at pH 7 followed by bioautograph on *S. aureus* gives a zone of inhibition at +2.5 cm.

EXAMPLE 15

Preparation of N-(bromo-t-butoxycarbonyl(thienamycin Step A

Preparation of N-(bromo-t-butoxycarbonyl)-O-Trimethylsilylthienamycin Trimethylsilyl Ester

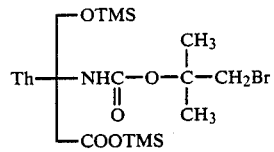

Th(TMS)$_3$ (16 mg.) obtained as above is dissolved in 0.4 ml of dry tetrahydrofuran to which is added 20 μl (28 mg., 0.13 mmol) of bromo-t-butylchloroformate (b.p. 35°/0.9 mm) and 8 μl (5.67 mg., 0.057 mmol) of triethylamine (redistilled from BaO). The mixture is shaken at 25° C. for 20 min. Evaporation of solvent and excess reagents gives desired product. UV$\lambda_{max}^{EtOAc}$ 320 nm (ε9,000).

Step B

Preparation of N-(bromo-t-butoxycarbonyl)thienamycin

N-bromo-t-butoxycarbonyl-O-trimethylsilylthienamycin trimethylsilyl ester (3 mg.) is dissolved in 0.1 ml. of tetrahydrofuran to which is added 0.5 ml. of 0.1M pH 7.0 phosphate buffer. The solution is left at 25° C. for 20 minutes and is then passed down a column (5 ml.) of

EXAMPLE 16

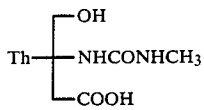

N-(Methylcarbamyl)thienamycin

O,N-Bistrimethylsilylthienamycin trimethyl silyl ester, [Th(TMS)₃ prepared by Example 9] from 66 mg (0.24 mmoles) of Thienamycin is dissolved in 5 ml. of dry tetrahydrofuran. The solution is stirred at 25° C. and 80 mg. (1.1 mmoles) of redistilled methyl isocyanate is added. After 1 hour the IR spectrum of the tetrahydrofuran solution shows bands at 6.0μ (—N-H—CO—NH—) and 6.5μ (—NH—). The reaction solution is evaporated to dryness to remove the excess methyl isocyanate. The residue is dissolved in 5 ml. of dry tetrahydrofuran and again evaporated to dryness. The residue is dissolved in 5 ml. of 0.1N pH 7.0 sodium phosphate buffer and chromatographed on a column of 80 ml. of Dowex 50W×8 (Na⁺) using deionized water as eluant. Fractions of 8 ml. are taken at a rate of 8 ml./5 min. and the column effluent is monitored by UV absorption and refractive index. The product is located in fractions 4 to 9 which are combined and concentrated to a volume of 12 ml. The concentrate is chromatographed on a column of 80 ml. of XAD-2 resin using deionized water as the eluent. Fractions of 8 ml. are taken every 5 min. and the column is monitored by UV absorption and refractive index. Aliquots (size based on UV absorption) of fractions 11, 15, 17, 20, 22, 25 and 30 are subjected to paper electrophoresis at 50 v/cm for 15 mins. using 0.5M pH 7.0 phosphate buffer. The paper strips are evaluated using agar plates containing *S. aureus*. Zones characteristic of starting material Thienamycin which show virtually no electrophoresis mobility at pH 7.0 are absent from all fractions tested whereas zones for N-(methylcarbamyl)thienamycin are observed in fractions, 11, 15, 17, 20, 22, 25, and 30 to about 3.5 cm from the origin toward the anode. Fractions 14 to 35 are combined (158 ml.) and concentrated to a volume of about 20 ml. A sample of the 150 ml. of solution diluted 1:4 with water gives a UV max at 303 nm; A=1.38. The solution is freeze dried to yield 29.8 mg. of the desired derivative. λMax 303 nm Et=285.

The nmr spectrum (D₂O) of N-(methylcarbamyl)-thienamycin shows, in addition to resonances expected for the other functions, a singlet at δ2.88 for the CONHCH₃ moiety.

EXAMPLE 17

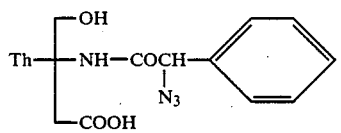

N-(α-Azidophenylacetyl)thienamycin

A solution of 39 mg. (0.14 mmole) of Thienamycin in 10 ml. of dioxane-water (1:1) is treated with 176 mg. (2.1 mmoles) of NaHCO₃ and cooled to 0° C. A 100-μl portion of a solution of 295 mg. of α-azidophenylacetyl-chloride in dioxane (total volume 0.5 ml.) is added with rapid stirring. After 15 min., two additional 50-μl portions of the α-azidophenylacetyl chloride solution are added at 15 min. intervals. Fifteen minutes after the final addition of the acid chloride, the reaction mixture is extracted with two 5 ml. portions of ether; 15 ml. of ethyl acetate is added to the aqueous phase which is rapidly stirred and acidified to pH 2.2–2.5 with phosphoric acid. The ethyl acetate layer is separated and the aqueous phase is washed with 5 ml. of ethyl acetate. The combined ethyl acetate solution is dried (MgSO₄), and after removal of the drying agent, 20 ml. of water is added. The N-(α-azidophenylacetyl)thienamycin is extracted into the aqueous layer by adding 103 mg. of NaHCO₃ at 0° C. with stirring. The aqueous layer is separated and the pH is adjusted to 7.2 by adding small amounts of NaHCO₃.

A 0.5 ml. sample is diluted with 2.5 ml. of D₂O and freeze-dried for nmr spectral analysis. Resonances at δ 5.0 and 7.48 are characteristic of the

and C₆H₅ moieties.

EXAMPLE 18

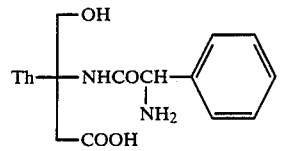

N-(α-Aminophenylacetyl)thienamycin

A water solution (6 ml.) of 6 mg. of N-(α-azido-phenylacetyl)-Thienamycin is stirred with 60 mg. of 10% Pd/C catalyst at 25° C. for 30 min. in an atmosphere of hydrogen. The reaction mixture is filtered through Supercel which is washed with nine 1-ml portions of water. The filtrate and washings are combined (15 ml.) and a 4 μl sample is subjected to electrophoresis on paper in pH 7 buffer at 50 v/cm for 15 min. The electrophoresis is evaluated by bioautograph on MB-108 agar plates and shows bioactive zones at ±0.5 cm (dia. 32 mm) for N-(α-aminophenylacetyl)-Thienamycin; +3.0 cm (dia. 16 mm) for N-(α-azidophenylacetyl)-Thienamycin; and +4.5 cm (dia. 22 mm) for a by product.

EXAMPLE 19

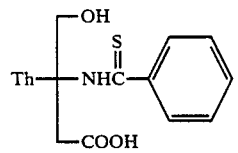

N-(Thiobenzoyl)thienamycin

A solution of 55.8 mg. (0.2 mmole) of Thienamycin in 18 ml. of dioxane-water (1:1) is treated with 263 mg. (3.1 mmoles) of $NaHCO_3$ and cooled to 0° C. Two 200-µl portions of a solution of 100 mg. of thiobenzoyl chloride in 0.6 ml. of dry dioxane are added to the rapidly stirred reaction solution at 15 min. intervals. Each portion of acid chloride solution contains 0.2 mmole of thiobenzoyl chloride. Fifteen minutes after the second addition, the reaction solution is washed with two 8-ml. portions of ether. Ethyl acetate (8 ml.) is added to the aqueous phase which is adjusted to pH of 2.2 at 0° C. with rapid stirring using 20% $H_3PO_4$. The layers are separated and the aqueous layer is washed with 3 ml. of ethyl acetate. The combined ethyl acetate layers are dried ($MgSO_4$). After separation of the drying agent, 10 ml. of water is added to the ethyl acetate solution and the product is extracted into the aqueous phase by adding 50 mg. (0.62 mmole) of $NaHCO_3$ with stirring at 0° C. (pH 7.4). The layers are separated and an aqueous phase containing N-(thiobenzoyl)thienamycin sodium salt is obtained, and freeze dried. Nmr in $D_2O$: $\delta 7.3-7.9$ characteristic of athe $C_6H_5SC$-moiety.

EXAMPLE 20

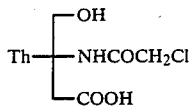

N-(Chloroacetyl)thienamycin

A solution of 94 mg. (0.34 mmole) of Thienamycin in 15.75 ml. of water and 6.75 ml. of distilled tetrahydrofuran is treated with 420 mg. (5.2 mmoles) of $NaHCO_3$ and cooled to 0° C. Three 100 µl portions of a solution of 390 mg. of chloroacetyl chloride in 1 ml. of dry tetrahydrofuran are added to the reaction solution at 15 min. intervals. Each portion of acid chloride solution contains 0.34 mmoles of chloroacetyl chloride. Fifteen minutes after the third addition, the reaction solution is washed with three 10-ml portions of ether. The aqueous layer is concentrated to a volume of about 10 ml. to remove last traces of organic solvents. The residual solution is chromatographed on 75 ml. of XAD-2 resin using water as the eluant at a rate of 8 ml./5 min. Electrophoresis of sample from selected fractions followed by bioautography indicates that product is present in fractions 16 through 47. These same fractions contain in addition variable amounts of unreacted Thienamycin. Fractions 16 through 47 are combined (250 ml.) and concentrated to a volume of 20 ml. The concentrate is chromatographed on 150 ml. of Ag 50×2 ($Na^+$) resin using deionized water at eluant at a rate of 8 ml./4 min. Samples of selected fractions are subjected to paper electrophoresis followed by bioautography against *S. aureus* MB 10% organisms. Product, uncontaminated by starting Thienamycin, is located in fractions 9 through 12. These fractions are combined to give 37 ml. of an aqueous solution of N-(chloroacetyl)-Thienamycin.

A 2 ml. sample is concentrated to 1 ml., diluted with 5 ml. of $D_2O$ and freeze-dried for determination of the nmr spectrum. A resonance at 4.22 $\delta$ is characteristic of the $ClCH_2CO$ moiety.

EXAMPLE 21

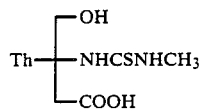

N-(Methylthiocarbamyl)thienamycin

O,N-Bistrimethylsilylthienamycin trimethylsilyl ester, [Th(TMS)$_3$ prepared by Example 9] from 66 mg. (0.28 mmoles) of thienamycin is dissolved in 5 ml. of dry tetrahydrofuran and to the solution is added 30 mg. of bis-trimethylsilyl trifluoroacetamide followed by 50 mg. (0.68 m-moles) of methylisothiocyanate. Samples (10 µl) of the reaction solution are added to pH 7.0 phosphate buffer (90 1, 0.1N) at intervals for evaluation by electrophoresis (at 50 v/cm for 15 min. at pH 7 phosphate buffer and the strips are evaluated by bioautography using *S. aureus* agar plates).

The zones observed at 4.2 cm. toward the anode are characteristic of N-(methylthiocarbamyl)thienamycin. The product is obtained by evaporating the reaction solution to dryness and dissolving the residue in 5 ml. of 0.1N phosphate (pH 7.0) buffer which removes the remaining silyl blocking groups and isolated by standard chromatographic techniques.

EXAMPLE 22

Preparation of N-Trimethylammoniumacetylthienamycin

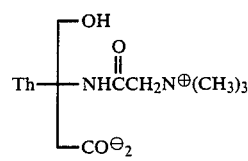

N-Bromoacetylthienamycin Sodium salt (20 mg.) is dissolved in water (2 ml.) containing trimethylamine hydrochloride. Dipotassium hydrogen phosphate is added to bring the solution to pH 8 and the mixture is kept at 4° C. for 20 hours. The mixture is evaporated under vacuum to a semisolid. The residue is redissolved in 10 ml. of water and the pH is readjusted to 8 by the addition of sodium hydroxide solution. The process of evaporation which serves to remove excess trimethylamine is repeated. The solution is applied to a column containing 25 ml. of a sulfonated polystyrene resin (Dowex 50) in the sodium cycle and the column is eluted with water. The first 20 ml. of eluant is discarded and the next 100 ml. is concentrated and freeze dried, yielding 5 mg. of a light powder consisting of N-trimethylammoniumthienamycin. UV$\lambda_{max}$ 301 nm (Et 117). Electrophoresis at 50 v/cm, pH 7, 20 minutes followed by bioautography shows a major zone of inhibition moving 1 cm. toward the cathode.

EXAMPLE 23

Preparation of N-(Sodiumthiosulfatoacetyl)thienamycin

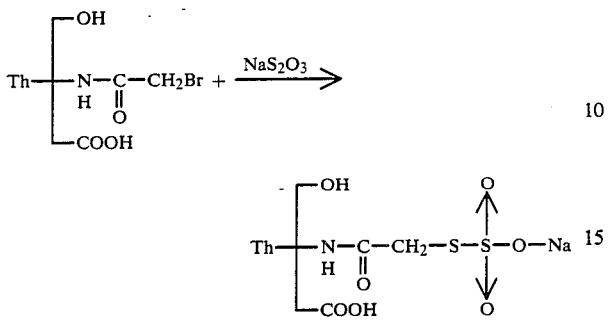

A solution of Sodium N-bromoacetylthienamycin (84 mg.) in 20 ml. of water is treated with 20 ml. of 0.1N Sodium thiosulfate and the mixture is allowed to stand at 4° C. for 10 hours. The solution is concentrated to 10 ml. and applied to a column (230 ml.) of XAD-2 resin. The column is eluted with water and the fractions are monitored by U.V. absorbance and refractive index. The correct fractions are combined and lyophilized to give the desired product: (75 mg. U.V.$\lambda_{max}$ 302 nm Et 89).

Electrophoresis of a sample (at 50 V/cm., pH 7, 20 minutes) shows a bioactive zone which moves 9 cm. toward the anode.

EXAMPLE 24

Preparation of N-o-nitrobenzenesulfenylthienamycin

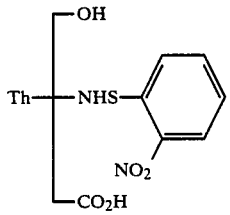

To a cooled solution of Thienamycin (2.4 mg.) in 1.5 ml. of 0.05M, pH 7, phosphate buffer and 0.75 ml of dioxane is added to a solution of o-nitrobenzenesulfenyl chloride (10 mg.) in 0.75 ml. dioxane. The pH is maintained at 0.2 by the addition of 0.1N sodium hydroxide. After 10 mins. the solution is adjusted to pH 7 with dilute hydrochloric acid and is extracted 3 times with ether. The aqueous solution is freeze dried to yield the sodium salt of N-orthonitrobenzenesulfenylthienamycin. Electrophoresis at 50 v/cm, pH 7 for 20 minutes followed by bioautography gives a single zone of inhibition at 2.5 cm toward the anode.

EXAMPLE 25

Preparation of p-Bromobenzoylthienamycin

Thienamycin (45.6 mg.) is dissolved in a mixture of 0.05M pH 7 phosphate buffer (4 ml.) and dioxane (2 ml.) and the solution is brought to pH 8.2 with 0.2N NaOH in 1:1 dioxane water. The solution is cooled to −8° C. and p-bromobenzoyl chloride (45 mg.) in dioxane (2 ml.) is added during 3 min. The pH is maintained between 7.6 and 8.4 by the addition of 0.2N NaOH for an additional 10 mins. The solution is neutralized to pH 7 and extracted 3 times with 8 ml. portions of ether. The aqueous phase is freeze dried to provide the sodium melt of N-p-bromobenzoylthienamycin, UV$\lambda_{max}$ 303 nm, 866 ODU. Electrophoresis at 50 v/cm, pH 7, for 20 mins, followed by bioautography shows a 22 mm. diameter zone of inhibition at −0.5 cm corresponding to Thienamycin and at 41 mm. diameter zone at +2.5 cm corresponding to the title compound.

EXAMPLE 26

Preparation of N-p-Guanidinophenylacetyl Thienamycin

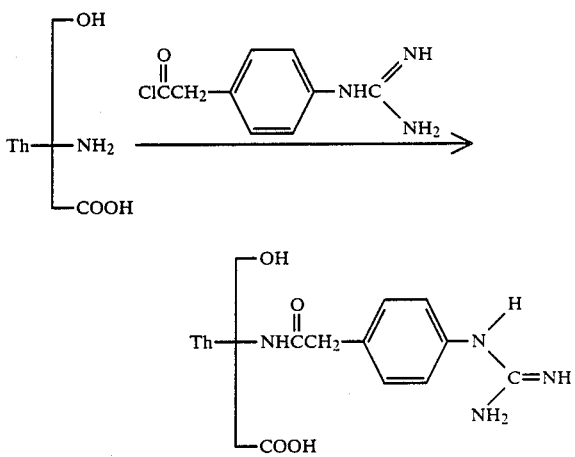

Thienamycin (60 mg) is dissolved in pH 7.0 phosphate buffer (0.05N, 6 ml.) and thoroughly cooled in an ice bath. The solution is then adjusted to pH 8.3 using a dispensing autoburette with 1.0N NaOH. To the stirred solution is added p-guanidinophenylacetyl chloride hydrochloride (64 mg., 259 μmol) in several portions so as to allow the autoburette to maintain a pH near 8.3. After a few minutes the reaction solution is acidified (10% H$_3$PO$_4$ solution) to pH 7.0 and chromatographed on 60 g XAD-2 resin. The column is eluted with water followed by 10% aqueous tetrahydrofuran solution which elutes product. The product fractions are combined and freeze-dried to give a white fluffy solid product (45 mg., $\lambda$max. 301 nm ($\epsilon$ 7, 020)). The product has an electrophoretic mobility of 2.5 cm towards the anode at 50 V/cm for 25 min. The nmr is consistent with that expected for product. The ir (Nujol mull) shows a band at 1775 cm$^{-1}$ ($\beta$-lactam).

EXAMPLE 27

Preparation of N-Pyridiniumacetyl Thienamycin

A mixture of 10 mg. of N-bromoacetyl thienamycin sodium salt and 0.5 ml. of pyridine in 1 ml. of HMPA is stirred for four hours at 25° C. The excess pyridine is removed under reduced pressure and the residue is taken up in 3 ml. of water and applied to a column of 20 ml. of XAD-2 resin. After elution with water the product is eluted with 10% aqueous THF. The solution has an optical density of 93 at $\lambda$max 261 nm and 71 at $\lambda$max. 297 nm. Electrophoresis and bioautography shows a major zone of inhibition at −1 cm corresponding to the desired product, N-pyridiniumacetyl Thienamycin.

EXAMPLE 28

Preparation of N-Carbomethoxy Thienamycin

Thienamycin (49 mg.) is dissolved in 0.05M pH 7.0 phosphate buffer (14 ml.) and cooled in an ice bath. With stirring the pH is adjusted to 8.2 using an automatic burette. A solution of methyl chloroformate (46 µl, 600 µmol) in p-dioxane (580 µl) is added at once to give a homogenous solution. Subsequently, the pH is maintained at 8.2 using the automatic burette. After 10 min., the solution is adjusted to pH 7.0 using dilute phosphoric acid solution and washed three times with an equal volume of diethyl ether. The aqueous solution is then concentrated to 4.5 ml. and chromatographed on an XAD-2 resin column. The product eluted (after water elution) with an aqueous 5% tetrahydrofuran solution and is freeze-dried to give 28.9 mg. of product. UV (pH 7.0 phosphate buffer 0.1N) $\lambda$max 303 nm ($\epsilon$ 6,450) Electrophoresis (20 min., 0.1N pH 7.0 phosphate buffer 50 v/cm) mobility 3.5 cm to cathode.

EXAMPLE 29

Preparation of N-Benzenesulfonyl Thienamycin

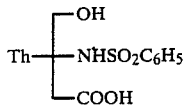

Thienamycin (52 mg.) is dissolved in pH 7.0 1N phosphate buffer (25 ml.) and magnetically stirred in an ice bath. The pH is adjusted to 8.2 with 2.5N NaOH using an automatic dispensing burette and benzenesulfonyl chloride (227 µl, 226 µmol) in 500 ml. p-dioxane) added at once. The pH is maintained at 8.2 (using the automatic burette) for 30 min. and then adjusted to pH 7.0 using dilute aqueous phosphoric acid. The reaction solution is concentrated to 15 ml. and chromatographed on XAD-2 resin (50 cc). The column is eluted with water, then followed with 10% aqueous tetrahydrofuran which elutes product. The 10% aqueous tetrahydrofuran eluate was concentrated to ⅓ volume and freeze dried to give 28 mg. Electrophoretic mobility of the product (50 v/cm, 20 min., pH 7 0.05N phosphate buffer) is 3.5 cm towards the cathode. $\lambda$max 303 ($\epsilon$ 3,650) in pH 7 0.1N phosphate buffer).

EXAMPLE 30

Preparation of N-Guanylthioacetyl Thienamycin

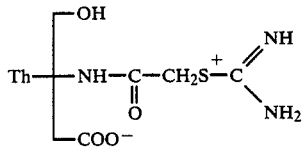

A solution of 90 mg. of sodium N-bromoacetyl Thienamycin in 40 ml. of water is adjusted to pH 6 and 36 mg. of thiourea is added. The solution is kept at 4° C. for five days. The solution is chromatographed on 80 ml. of XAD-2 resin. Elution with 400 ml. water removes thiourea, and a small amount of the starting bromo acetyl derivative and Thienamycin. Elution with 120 ml. of 10% tetrahydrofuran gives a solution containing the N-guanylthioacetyl derivative of Thienamycin. High pressure liquid chomatographic analysis on Bondapak C18 porasil with 10% THF solvent shows a major peak of 90% purity. The solution is evaporated to 15 ml. (pH 5.5) and freeze-dried. Yield, 40 mg. of white powder. U.V. $\lambda$max 299 E% 173.

EXAMPLE 31

Preparation of Thienamycin N-(S-Phenylcarbothioate) Sodium Salt

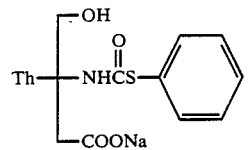

To Thienamycin (37 mg., 0.14 mmole) in 24 ml. 1:1 dioxane-H₂O at 0° C., is added while stirring 150 mg. (1.78 mmoles, 12 eq) of NaHCO₃, and then, dropwise with stirring over 4 min., 1.5 equivalents (39 mg., 0.22 mmole) of phenyl chlorothioformate in 0.6 ml. dioxane. After 15 min. the pH is adjusted to 5.9 with aqueous 25% H₃PO₄ and the solution extracted with ether. The aqueous layer after removing any entrained ether in vacuo is then brought to pH 2.5 at 0° C. and extracted with EtOAc. The ethylacetate extracts are combined and quickly backwashed with cold brine, dried over MgSO₄, filtered and back extracted with water containing 1.5 equivalents of NaOH to a final pH of 6.8. The aqueous layer is freed from any EtOAc in vacuo and lyophilized. The aqueous solution contains 486 ODU at 302 nm (UV analysis in H₂O at pH 7.0) which is 95% extinguished after treatment with hydroxylamine for one hour. The yield is 17.7 mg. (29%). Electrophoresis (50 v/cm for 18 min., pH 7.0 aq phosphate, 0.05M) shows one spot by bioautograph, 3.6 cm toward the anode.

EXAMPLE 32

Preparation of Thienamycin N-(O-Phenylcarbothioate) Sodium Salt

To Thienamycin (46.5 mg., 0.17 mmoles) in 26 ml. 1:1 dioxane-H₂O at 0° C., is added while stirring 220 mg. (2.62 mmoles, 15 equiv.) of NaHCO₃, and then dropwise over 4 min., 1.5 equivalents of phenoxythiocarbonyl chloride in 0.6 ml. dioxane. After 8 min. the pH is adjusted to 7.0 and then the solution extracted with ether. The aqueous layer, after removing any entrained ether in vacuo, is then brought to pH 2.5 at 0° C., and extracted with EtOAc. The ethyl acetate extracted are combined, quickly backwashed with cold brine, dried over MgSO₄, filtered and back extracted with water containing 1.5 eq of 0.1M NaOH to a final pH of 6.8. The aqueous layer is freed from any EtOAc in vacuo and lyophilized. The aqueous solution contains 572 ODU at 302 nm (UV analysis in H₂O at pH 7.0) which is 95% extinguished after treatment with hydroxylamine for 1 hour. The yield is 19 mg. (26% of theory). Electrophoresis (50 v/cm for 18 min., pH 7 aq phosphate, 0.05M) shows one spot by bioautography, 3.3 cm toward the anode.

EXAMPLE 33

Preparation of N-(Dimethoxyphosphinothioyl)Thienamycin Sodium Salt

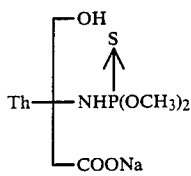

To the trimethylsilyl derivative, Th(TMS)$_3$, prepared from 214 mg. of Thienamycin in 25 ml dry THF is added 227 mg dimethylphosphorochloridothionate in 2 ml THF followed by 0.10 ml (130 mg) of triethylamine. After stirring under dry nitrogen for approximately 2 hours, the contents is concentrated to a viscous residue in vacuo. The pasty residue is suspended in 40 ml ethylacetate containing 5 ml deionized water and the pH brought to 3.5 with dilute aqueous phosphoric acid and stirred for 10 minutes. The aqueous layer is separated and extracted with 2×20 ml ethylacetate (EtOAc). The EtOAc extracts are combined, quickly dried with anhydrous MgSO$_4$ and filtered. To the cold EtOAc extract is added 20 ml of water and the pH brought to 7 with dilute NaOH. The aqueous layer is separated and concentrated in vacuo to a smaller volume (7 ml) and placed on a 35×4 cm column containing 500 ml of an XAD-2 resin. The column is eluted with H$_2$O followed by 6% aqueous THF and finally 10% aqueous THF. The fraction eluted with 10% THF (tubes 99–150, 14 ml/tube) has a $\lambda_{max}$ 304 nm and contains the desired product. Electrophoresis (50 v/cm, 16 min. pH 7 aq. phosphate, 0.05M) exhibits one zone only by bioautograph (MB-108 *Staph. aureus*)3 cm towards the anode. Lyophilization gives 39 mg (10.5% yield) of N-(dimethoxyphosphinothioyl)Thienamycin Sodium Salt. NMR (D$_2$O) 4.0 (d, J=.10 Hz.P-OCH$_3$)

EXAMPLE 34

Preparation of N-(Dimethoxyphosphinyl)Thienamycin Sodium Salt

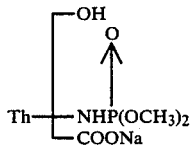

To the trimethylsilyl derivative Th(TMS)$_3$ prepared from 93 mg of Thienamycin in 2 ml dry THF is added 88 mg dimethylphosphorochloridate in two portions followed by 45 g (0.06 ml) of triethylamine. After stirring vigorously for 1 hour the contents is concentrated to a viscous residue in vacuo. The residue is suspended in 10 ml EtOAc and 3 ml of pH 3 phosphate buffer added and stirred for 10 min. The aqueous layer is separated and extracted with 2×3 ml EtOAc. The EtOAc extracts are combined, dried with anhydrous MgSO$_4$ and filtered. To the cold EtOAc extract is added 6 ml H$_2$O and the pH brought to 7 with dilute NaOH. The aqueous layer is separated and concentrated in vacuo to provide 18 mg (13% yield) of N-(dimethoxyphosphinoyl)thienamycin sodium salt; $\lambda_{max}$ 303 nm; Electrophoresis (50 v/cm, 20 min pH 7 aq. phosphate 0.05M) exhibits one zone 3.2 cm towards the anode (bioautograph MB-108 *staph. aureus*.) NMR (δ, D$_2$O) ~4.0 (d 5=10 Hz POCH$_3$).

EXAMPLE 35

Preparation of N-(Bis(methylthio)phosphinothioyl)Thienamycin Sodium Salt

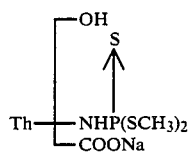

To the trimethylsilyl derivative Th(TMS)$_3$ prepared from 213 mg of Thienamycin in 20 ml of dry THF is added 300 mg of dimethylphosphorochloridotrithioate in 2 ml of THF followed by 0.18 ml (130 mg) of triethylamine. After stirring under dry nitrogen for 3 hours, the contents is concentrated to a viscous residue in vacuo. The pasty residue is suspended in 25 ml EtOAc containing 5 ml of H$_2$O and the pH brought to 3.5 with dilute aqueous phosphoric acid and stirred for 10 minutes. The aqueous layer is separated and extracted with 2×10 ml EtOAc. The EtOAc extracts are combined dried with anhydrous MgSO$_4$ and filtered. To the cold EtOAc extract is added 5 ml of H$_2$O and the pH brought to 7 with dilute NaOH. The aqueous layer is separated and concentrated in vacuo to a smaller volume (7 ml) and placed on a 30×3 cm column containing 150 ml of XAD-2 resin. The column is washed with H$_2$O followed by aq. 9% THF which removes the product N-(Bis(methylthio)phosphinothioyl)thienamycin sodium salt ($\lambda_{max}$ 306 nm) which is then lyophilized to give 69 mg of a yellow-light orange solid (19.6%). Electrophoresis (50 V/cm, 20 min. pH 7 aq phosphate, 0.05M) exhibits one zone 3 cm towards the anode (bioautograph MB-108 *Staph aureus*).

EXAMPLE 36

Preparation of N-Sulfamoyl Thienamycin Sodium Salt

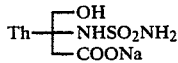

To the trimethylsilyl derivative Th(TMS)$_3$, prepared from 210 mg of Thienamycin in 20 ml THF is added 223 mg of sulfamoyl chloride in 5 ml of THF followed by 0.25 ml (180 mg) of triethylamine. After stirring under dry nitrogen for 2 hours, the mixture is concentrated to a viscous residue, in vacuo. The pasty residue is suspended in 50 ml EtOAc containing 5 ml H$_2$O and the pH brought to 3.5 and stirred for 10 min. The aqueous layer is separated and extracted 1×10 ml EtOAc. The EtOAc extracts are combined dried with anhydrous MgSOy and filtered. To the cold EtOAc extract is added 18 ml H$_2$O and the pH adjusted to 7.0 with dilute NaOH. The aqueous layer is separated and concentrated in vacuo to a smaller volume and placed on a 33×4 cm column containing 500 ml XAD-2 resin. The column is eluted with H$_2$O to provide N-Sulfamoyl thienamycin sodium salt. $\lambda_{max}$ 303 nm Electrophoresis (50 V/cm 20 min pH 7 aq phosphate buffer 0.05M)

exhibits one zone 3.2 cm toward the (bioautography MB108, *Staph aureus*). Lyophilization of the above solution gives 90 mg (41%) of N-sulfamoyl thienamycin sodium salt as a yellow solid. IR Nujol β-lactam C=O 1750 shoulder 1770 (5.71+5.65μ) and 1150 cm$^{-1}$ (8.65μ) for HN—SO$_2$NH$_2$.

EXAMPLE 37

Preparation of N-(β-Azidopropionyl)Thienamycin

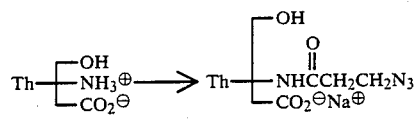

Thienamycin (184 mg) is dissolved in 30 ml of water and is kept at 0° C. To the solution is added 0.52 g of NaHCO$_3$, 30 ml of dioxane and 163 mg of β-azidopropionyl chloride. The mixture is stirred for 15 minutes then is neutralized with 30% H$_3$PO$_4$, extracted with ether. The aqeuous layer is separated and concentrated to 5 ml. The crude product is chromatographed on a Dowex 50W×8 (Na form) ion-exchange column (1″×10″). The column is eluted with H$_2$O to give 81 mg of the desired product which shows uv absorption at $\lambda_{max}^{H2O}$ 306 nm. Electrophoresis of the product at 2 KV in 0.1M pH 7.0 phosphate buffer for 2 hours shows a single bioactive zone which moves 30 mm toward anode.

EXAMPLE 38

Preparation of N-(β-Alanyl)Thienamycin

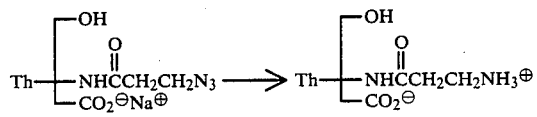

The aqueous solution of N-(β-azidopropionyl)-Thienamycin (40 mg in 20 ml water) is hydrogenated under 1 atm of hydrogen in the presence of 200 mg of palladium at 25° C., for 40 minutes. The resultant solution (pH 9.0) is neutralized with 30% H$_3$PO$_4$ and filtered from the catalyst. The mixture is chromatographed on a Dowex 50W×8 (Na form) ion-exchange column (1″×10″) and the column is eluted with water to give 20 mg of the desired product which shows uv $\lambda_{max}^{H2O}$ 302 nm. Electrophoresis of the product at 2 KV in 0.1M pH 7.0 phosphate buffer for 20 mins shows single bio-active zone which moves 10 mm toward cathode.

EXAMPLE 39

Preparation of N-[N′-Acetimidoyl-β-Alanyl]Thienamycin

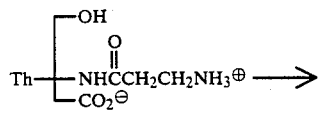

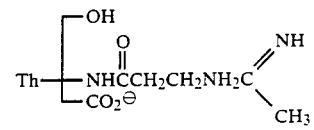

The aqueous solution of N-(β-alanyl)thienamycin (125 mg in 15 ml water) is kept at 0° C. and maintained at pH 8.5 by adding 2.5N NaOH while O-ethylacetimidate hydrochloride (350 mg) is added portionwise to the solution during a period of 10 min. The mixture is stirred for 1 hour then is neutralized with 2.5N HCl and concentrated to 15 ml. The crude product so obtained is chromatographed twice on Dowex 50W×8 (Na form) column (1″×10″) to yield 25 mg. The prouct is eluted with water and the solution lyophilized. Recrystalization of the product from water gives a crystalline solid which shows ir (Nujol mull): 1769 cm$^{-1}$ (β-lactam); nmr (D$_2$O,$_H$2O 100 MHz): 2.20 ppm (s, acetimidoyl CH$_3$); uv $\lambda_{max}^{H2O}$ 302 nm. Electophoresis of the product at 2 KV in 0.1M pH 7.0 phosphate buffer for 20 min shows a single bio-active zone which moves 10 mm toward cathode.

EXAMPLE 40

Following the procedures described in Examples 37, 38, 39 except that:

1. O-ethyl acetimidate hydrochloride is replaced by an equivalent amount of O-methylformimidate hydrochloride in Example 39;
2. β-azidopropionylchloride is replaced by an equivalent amount of azidoacetylchloride in Example 37;
3. N-(β-azidopropionyl)thienamycin is replaced by an equivalent amount of N-(azidoacetyl)thienamycin in Example 38;
4. N-(β-alanyl)thienamycin is replaced with an equivalent amount of N-glycyl thienamycin in Example 39;
5. O-ethyl acetimidate hydrochloride is replaced with an equivalent amount of O-methyl formimidate hydrochloride and N-(β-alanyl)thienamycin is replaced with N-glycyl thienamycin in Example 39;
6. O-ethyl acetimidate hydrochloride is replaced with an equivalent amount of methyl sulfate in Example 39;
7. O-ethyl acetimidate hydrochloride is replaced with an equivalent amount of methyl sulfate and N-(β-alanyl)thienamycin is replaced with N-glycyl thienamycin in Example 39; and
8. N-(β-azidopropionyl)thienamycin is replaced with an equivalent amount of N-(2-azidoethoxylcarbonyl)-thienamycin in Examples 38.

There is obtained the compounds enumerated in the table below:

| Compound | m | n | A | Y |
|---|---|---|---|---|
| (1.) | 1 | 1 | — | $-\overset{\oplus}{N}H_2\overset{\overset{NH}{\|}}{C}-H$ |
| (2.) | 1 | 0 | — | $-N_3$ |

-continued

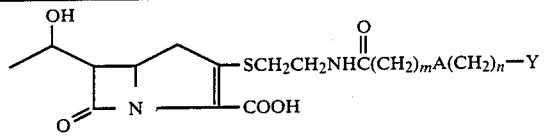

| Compound | m | n | A | Y |
|---|---|---|---|---|
| (3.) | 1 | 0 | — | $-\overset{\oplus}{N}H_3$ |
| (4.) | 1 | 0 | — | $-\overset{\oplus}{N}H_2-\overset{\overset{NH}{\|\|}}{C}-CH_3$ |
| (5.) | 1 | 0 | — | $-\overset{\oplus}{N}H_2-\overset{\overset{NH}{\|\|}}{C}-H$ |
| (6.) | 1 | 0 | — | $-\overset{\oplus}{N}(CH_3)_3$ |
| (7.) | 1 | 0 | — | $-\overset{\oplus}{N}(CH_3)_3$ |
| (8.) | 0 | 2 | Oxygen | $-\overset{\oplus}{N}H_3$ |

EXAMPLE 41

Preparation of N-phenoxyacetyl thienamycin Sodium Salt

To a 250 ml flask containing thienamycin (190 mg) is added 30 ml of water, 0.6 g of sodium bicarbonate and 30 ml of dioxane. While the mixture is stirred and kept at 0° C., phenoxyacetyl chloride (170 mg) is added dropwise to the flask during a period of 10 minutes. The solution is stirred for an additional 10 minutes and then acidified with 30% phosphoric acid to pH 4.5. The acidified solution is quickly extracted with 50 ml of ether to remove excess reagent and its hydrolyzed product phenoxyacetic acid. The aqueous layer so obtained is further acidified with 30% phosphoric acid to pH 2.0, and extracted with 50 ml of ethylacetate. The organic layer which contains the free acid of N-phenoxyacetyl thienamycin is separated and back extracted with 30 ml of aqueous solution containing 60 mg of sodium bicarbonate. The aqueous layer is freeze dried to yield 120 mg of N-phenoxyacetyl thienamycin sodium salt. Electrophoresis (0.5M, pH 7.0, phosphate buffer, 2 KV for 20 min): single bioactive zone which moves 45 mm toward anode. UV: $\lambda_{max}^{H_2O}$ 302 nm.

EXAMPLE 42

N-β-Guanidinopropionyl thienamycin

Step A: β-Guanidinopropionyl chloride hydrofluoride

β-guanidinopropionic acid (130 mg) is added in portions to 1 ml of thionyl chloride in a centrifuged tube under nitrogen. The pasty reaction mixture is rubbed with a glass rod until it becomes crystalline. The excess thionyl chloride is evaporated in a stream of nitrogen leaving a solid residue of β-guanidinopropionyl chloride hydrochloride. I.R. 5.6μ

broad band 6-6.3μ (guanidino).

Step B

Thienamycin (54 mg) is suspended in 1 ml of anhydrous dimethylformamide. The mixture is cooled to 0° and β-guanidinopropionyl chloride hydrochloride (37 mg) is added with stirring immediately followed by a solution of 25.8 mg of diisopropylethylamine in 0.1 ml of DMF. After an additional 5 minutes the product is precipitated with ether. The ether is decanted and the residue is dissolved in 2 ml of water, adjusted to pH 6.8 with sodium bicarbonate and chromatographed on 75 ml of XAD-2 resin. After elution with water the product is eluted with 10% aqueous THF, concentrated and freeze-dried. UV $\lambda_{max}$ 303 mμ E% 157. Electrophoresis (1 hr, 50 V/cm, pH 7) shows a single bioactive spot which moves 4.5 cm towards the cathode and gives a positive Sakaguchi color test.

EXAMPLE 43

Preparation of N-Guanylcarbamoyl Thienamycin

Thienamycin (253 mg) is dissolved in 0.1N pH 7 phosphate buffer (11 ml), cooled in an ice bath, and adjusted to pH 8.5 using 1N NaOH dispensed from an autoburette. To this solution is added a cold solution (2.5 ml) of 1-amidino-semicarbazide dihydrochloride (354 mg) and sodium nitrite (128 mg). The pH drifts to 9.0 and after 10 minutes the pH is adjusted to and maintained at 8.2. After 30 minutes, a precipitate forms and the pH is adjusted to 7.0 using 1N HCl. The mixture is filtered and the filtrate chromatographed on a column of XAD-2 resin (120 ml.) which is eluted with water followed by aqueous 10% tetrahydrofuran. The N-guanylcarbamoyl thienamycin derivative elutes in aqueous tetrahydrofuran and is lyophilized to a solid. UV (pH 7 0.1N phosphate buffer) $\lambda_{max}$ 298 nm (ε 5,500) HPLC C$_{18}$ Bondapak, aqueous 10% tetrahydrofuan) Retention time 2.0 times that of thienamycin. Electrophoresis (40 v/cm, pH 7 0.1N phosphate buffer, 20 min) mobility of 2 cm towards anode.

EXAMPLE 44

Following the procedures set out in the foregoing examples and text, the following compounds of the present invention are defined:

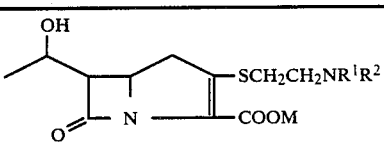

| Compound | M | R$^1$ | R$^2$ |
|---|---|---|---|
| (1.) | Na | H | $-\overset{\overset{O}{\|\|}}{C}-CH=CH_2$ |
| (2.) | Na | H | $-\overset{\overset{O}{\|\|}}{C}-CH_2O-C_2H_5$ |
| (3.) | Na | H | $-\overset{\overset{O}{\|\|}}{C}-NH_2$ |
| (4.) | H | H | $-\overset{\overset{O}{\|\|}}{C}-\overset{\overset{H}{\|}}{N}-CH_3$ |

-continued

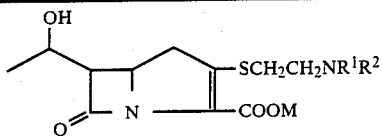

| Compound | M | R¹ | R² |
|---|---|---|---|
| (5.) | H | H | $-\underset{\underset{O}{\|}}{C}-CH_2N(CH_3)_2$ |
| (6.) | H | H | $-\underset{\underset{O}{\|}}{C}-CH_2-\underset{H}{N}-\underset{\underset{N}{\|}}{C}-NH_2$ (H on N) |
| (7.) | Na | H | $-\underset{\underset{O}{\|}}{C}-CH_2-S-CH_3$ |
| (8.) | Na | H | $-\underset{\underset{O}{\|}}{C}-CH(-OCH_3)_2$ |
| (9.) | Na | H | $-\underset{\underset{O}{\|}}{C}-CH_2OH$ |
| (10.) | Na | H | $-\underset{\underset{O}{\|}}{C}-C\equiv CH$ |
| (11.) | H | H | $-\underset{\underset{O}{\|}}{C}-CH_2\underset{H}{N}-\underset{\underset{O}{\|}}{C}-\underset{H}{N}-\underset{\underset{N}{\|}}{C}-NH_2$ (H on N) |
| (12.) | Na | H | $-\underset{\underset{O}{\|}}{C}-CHOHCH_3$ |
| (13.) | K | H | $-\underset{\underset{O}{\|}}{C}-CH(CH_3)_2$ |
| (14.) | NH₄ | H | $S-CF_3$ |
| (15.) | K | H | $-\underset{\underset{O}{\|}}{C}-H$ |
| (16.) | Na | H | tetrazolyl-CH₂-C(=O)- |
| (17.) | Na | H | triazolyl-CH₂-C(=O)- |
| (18.) | Na | H | phenyl-CH(triazolyl)-C(=O)- |
| (19.) | Na | H | $-\underset{\underset{O}{\|}}{C}CH_2SCH_2CN$ |
| (20.) | Na | H | $-CCH(NH_2)CH_3$ |
| (21.) | Na | H | $-SO_2CF_3$ |

-continued

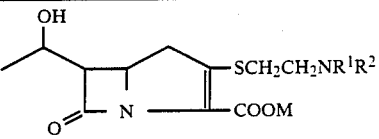

| Compound | M | R¹ | R² |
|---|---|---|---|
| (22.) | Na | H |  |

EXAMPLE 45

Preparation of Pharmaceutical Compositions

One such unit dosage form consists in mixing 120 mg. of N-glycylthienamycin with 20 mg. of lactose and 5 mg of magnesium stearate and placing the 145 mg. mixture into a No. 3 gelating capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| N—glycylthienamycin | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | |
|---|---|
| Ampoule: | |
| N—glycylthienamycin | 500 mg. |
| Sterile Water | 2 ml. |
| OPTHALMIC SOLUTION | |
| N—glycylthienamycin | 100 mg. |
| Hydroxypropylmethyl Cellulose | 5 mg. |
| Sterile Water to | 1 ml. |
| OTIC SOLUTION | |
| N—glycylthienamycin | 100 mg. |
| Benzalkonium Chloride | 0.1 mg. |
| Sterile Water to | 1 ml. |
| TOPICAL OINTMENT | |
| N—glycylthienamycin | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

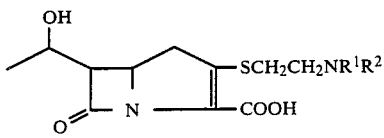

and the non-toxic, pharmaceutically acceptable salts thereof; wherein $R^1$ is hydrogen and $R^2$ is

type acyl wherein X is O or S, with the proviso that $R^2$ is not formyl or acetyl.

2. A compound according to claim 1 wherein the acyl radical is selected from the group consisting of:

wherein X is O or S;

R is H, amino, alkylamino, dialkylamino, alkyl, alkylthio, arylthio, alkoxy, aryloxy, alkenyl, alkynyl, aryl, aralkyl, cycloalkyl, heteroaryl, or heteroaralkyl.

3. A compound according to claim 1 wherein the acyl radical is selected from the group consisting of:

wherein X is O or S;

R is amino, mercapto, hydroxy, alkylamino, dialkylamino, alkyl, alkylthio, arylthio, alkoxy, aryloxy, alkenyl, alkynyl, aryl, aralkyl, cycloalkyl, heteroaryl, or heteroaralkyl.

n is an integer selected from 0, 1, 2, 3, or 4; Z is O, S, N or carbonyl; except that when Z is oxygen R is not mercapto or hydroxy; when Z is sulfur R is not amino or hydroxy; and when Z is nitrogen R is not mercapto.

4. A compound according to claim 1 wherein the acyl radical is selected from the group consisting of:

wherein X is O or S;

R is H, amino, mercapto, hydroxy, alkylamino, dialkylamino, alkyl, alkylthio, arylthio, alkoxy, aryloxy, alkenyl, alkynyl, aryl, aralkyl, cycloalkyl, heteroaryl, or heteroaralkyl;

R' is amino, hydroxy, azido, carbamoyl, guanidino, acyloxy, halo, sulfamino, tetrazolyl, sulfo, carboxy, carbalkoxy, phosphono, alkoxy, or arylthio; with the exception that both R' and R cannot both be hydroxy, amino, or mercapto.

5. A compound according to claim 1 wherein the acyl radical is selected from the group consisting of

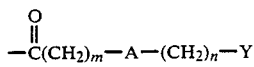

wherein m and n are integers selected from 0-5; A is O, NR' (R' is hydrogen or loweralkyl having from 1-6 carbon atoms), S or A represents a single bond; and Y is selected from the group consisting of:

amino or substituted amino: (1.)

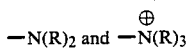

wherein the values for R are independently selected from: hydrogen; $N(R')_2$ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2-6 carbon atoms; cycloalkyl and cycloalkylalkyl wherein the cycloalkyl moiety comprises 3-6 carbon atoms and the alkyl moiety comprises 1-3 carbon atoms; two R groups may be joined together with the N atom to which they are attached to form a ring having 3-6 atoms;

amidino and substituted amidino: (2.)

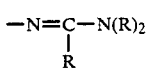

wherein the value of R is independently selected from the group consisting of: hydrogen; $N(R')_2$ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

guanidino and substituted guanidino: (3.)

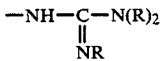

wherein R is as defined in 2. (above);

guanyl and substituted guanyl: (4.)

wherein R is as defined in 2. (above);

5. nitrogen-containing mono- or bicyclic heterocycles (aromatic and non-aromatic) having 4 to 10 nuclear atoms wherein the hetero atom or atoms, in addition to nitrogen, are selected from oxygen and sulphur.

6. A compound according to claim 2 wherein $R^1$ is hydrogen and $R^2$, the acyl radical, is:

wherein
R is selected from the group consisting of benzyl, p-hydroxybenzyl, 4-amino-4-carboxybutyl, methyl, cyanomethyl, 2-pentenyl, n-amyl, n-heptyl, ethyl, 3- and 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl) methyl, 2-furylmethyl, 2-(5-nitrofuryl)methyl, 3-furylmethyl, 2-thienylmethyl, 3-thienylmethyl, tetrazolylmethyl, benzamidinomethyl, and cyclohexylamidinomethyl.

7. A compound according to claim 3 wherein $R^1$ is hydrogen and $R^2$, the acyl radical, is:

wherein the moiety —(CH₂)ₙZR of the acyl radical is selected from the group consisting of allylthiomethyl, phenylthiomethyl, butylmercaptomethyl, α-chlorocrotylmercaptomethyl, phenoxymethyl, phenoxyethyl, phenoxybutyl, phenoxybenzyl,diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronapthyl)oxymethyl, N-methyl-N-pyridiniumthio, benzyloxy, methoxy, ethoxy, phenoxy, phenylthio, amino, methylamino, dimethylamin, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

8. A compound according to claim 4 wherein $R^1$ is hydrogen and $R^2$, the acyl radical, is:

wherein the moiety —CHRR' of the acyl radical is selected from the group consisting of α-aminobenzyl, α-amino-(2-thienyl)methyl, α-(methylamino)benzyl, α-amino-methylmercaptopropyl, α-amino-3- or 4-chlorobenzyl, α-amino-3 or 4-hydroxybenzyl, α-amino-2,4-dichlorobenzyl, α-amino-3,4-dichlorobenzyl D(−)-α-hydroxybenzyl, α-carboxybenzyl,α-amino-(3-thienyl)methyl, D-(−)-α-amine-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(−)-2-thienyl-guanidinomethyl, D(−)-α-guanidinobenzyl,α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4,(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxymethyl, 3-(1,2-thiazolyl)-aminomethyl, 3-(1,2-thiazolyl)-hydroxymethyl, 3-(1,2-thiazolyl)-carboxymethyl, 2-thiazolylaminomethyl, 2-thiazolylhydroxymethyl, 2-thiazolylcarboxymethyl, 2-benzothienylcarboxymethyl, 2-benzothienylhydroxymethyl, 2-benzothienylcarboxymethyl, α-sulfobenzyl, α-phosphonobenzyl, α-diethylphosphono, and α-monoethylphosphono.

9. A compound according to claim 5 wherein $R^1$ is hydrogen and $R^2$, the acyl radical, is selected from the group consisting of:

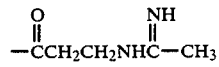

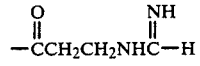

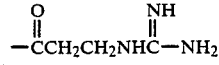

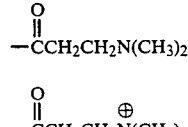

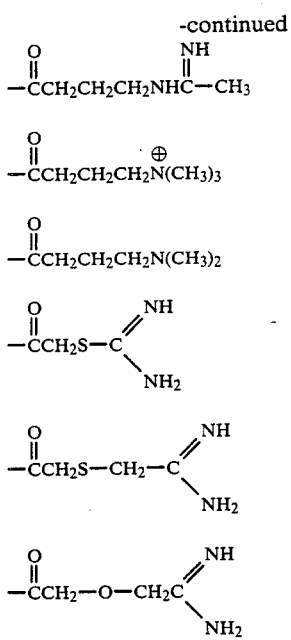

10. A pharmaceutical composition for antibiotic use comprising a therapeutically effective amount of a compound according to claim 1 and a pharmaceutical carrier therefor.

11. A pharmaceutical composition for antibiotic use comprising, in unitary dosage form, a therapeutically effective amount of a compound according to claim 1 and a pharmaceutical carrier therefor.

12. A compound according to claim 1 wherein $R^2$ is selected from the group consisting of: propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)aminopropionyl, N,N,N-triethylaminoacetyl, pyridiniumacetyl, guanylthioacetyl, guanidinoacetyl, 3-guanidinopropionyl, $N^3$-methylguanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)-propionyl, 3-(5-aminoimidazol-1-yl)propionyl, 3-methyl-1-imidazoliumacetyl, 3-sydnonylacetyl, o-aminomethylbenzoyl and o-aminobenzoyl.

* * * * *